United States Patent [19]
Adkins

[11] Patent Number: 5,172,424
[45] Date of Patent: Dec. 22, 1992

[54] APPARATUS FOR PROTECTION OF THE UNDER FINGER OF A QUILTER

[76] Inventor: Jean S. Adkins, Rt. 3, Box 433, Fayetteville, N.C. 28306

[21] Appl. No.: 646,464

[22] Filed: Jan. 25, 1991

[51] Int. Cl.⁵ ............................................. A41D 13/00
[52] U.S. Cl. ................................................ 2/21; 2/20; 2/160
[58] Field of Search ............... 2/21, 20, 160; 128/155; 294/25

[56] References Cited

U.S. PATENT DOCUMENTS

| | | | |
|---|---|---|---|
| 1,555,960 | 10/1925 | Fuller | 2/21 |
| 3,191,824 | 6/1965 | Burr | 2/21 |
| 3,283,888 | 11/1966 | Scott | 2/21 |
| 4,285,338 | 8/1981 | Lemelson | 128/155 |
| 4,694,508 | 9/1987 | Iriyama et al. | 2/160 |
| 4,858,245 | 8/1989 | Sullivan et al. | 2/21 |

*Primary Examiner*—Werner H. Schroeder
*Assistant Examiner*—Gloria Hale
*Attorney, Agent, or Firm*—Dickinson, Wright, Moon, Van Dusen & Freeman

[57] ABSTRACT

A protector for the under finger of a quilter is made from flexible vinyl having a slightly roughened upper surface and a thickness of about 13 mil. The back of the protector is provided with an adhesive so that it may be attached to the under finger easily. In the preferred embodiment, a number of protectors are provided on a strip from which a single protector may be detached.

3 Claims, 1 Drawing Sheet

APPARATUS FOR PROTECTION OF THE UNDER FINGER OF A QUILTER

TECHNICAL FIELD

This invention relates to quilting. In particular, the invention relates to the protection of the under finger of a quilter.

BACKGROUND

In the practice of quilting, a needle is pressed through material. The needle may be pressed through the material by a thimble or other device such as shown in my prior U.S. Pat. No. 4,534,495. A problem which has not been addressed, however, is that of the "under finger." The under finger is the finger placed under the quilt which receives the tip of the needle as it passes through the quilt. When the quilter feels the tip of the needle on the under finger, she pushes up to cause the needle to return to the top of the quilt, at which point it is again reversed in direction. An experienced quilter may be capable of doing this several times before actually pulling the thread through the quilt. It is also important that the needle pass through the material at the proper location, and this requires that the quilter feel the tip of the needle as it begins to emerge from the material. These operations require that the tip of the needle engage the under finger of the quilter, which in turn leads to injury of the under finger.

Devices which attach to the upper finger of one sewing or quilting are known, but these cannot be used on the under finger because they do not provide adequate feeling of the tip of the needle or adequate control of the needle tip.

U.S. Pat. No. 3,191,824 (Burr) shows a device comprising a dimpled disk of nylon attached to a piece of adhesive tape for being held to the finger of one sewing. The device is designed for engaging the eye end of the needle for pushing it through material and is not capable of allowing the one sewing to "feel" the needle.

U.S. Pat. No. 3,283,888 (Scott) shows a number of disks for attachment to the finger to provide an improved coefficient of friction. A plurality of disks are provided on a sheet, and each disk comprises a piece of foam rubber having a high coefficient of friction with paper.

U.S. Pat. No. 3,985,383 (Yonkers) shows another device for providing a high coefficient of friction with material to be indexed. The material is attached to the finger by adhesive, and the material is an elastomeric material which may comprise foam or sponge rubber containing glycerin or smooth rubber stock which has been hatched.

SUMMARY OF THE INVENTION

In accordance with the invention, a finger protector comprises a piece of material with an adhesive backing such that it may easily be attached to the under finger of a quilter. The finger protector has several properties which make it extremely useful for this purpose. The material of the finger protector is thin enough that it provides a good feel of the tip of the needle by the quilter but is thick enough that it protects the finger from injury. The tip does not penetrate the finger protector material to any great extent, is easily removed from the material if embedded, and the needle is easily deflected by the material and guided upward into the quilt.

It should be noted that the under finger is not generally used for pushing the needle through the material in the same manner as is normally accomplished with a thimble. The thimble is used on the eye end of the needle to push it through the quilt while the under finger deflects the tip of the needle.

In the preferred embodiment, the material used for the finger protector of the invention is flexible vinyl having a thickness of 13 mil. This material is also used for tags on trees and may be obtained from Economy Labels, P.O. Box 350, Daytona Beach, Fla. 32115, under catalog number FX 10-761. The thickness may vary by about ±10%.

The flexible vinyl is provided with an adhesive backing (e.g., double sided tape) and is scored to permit small pieces to be applied to the under finger.

DETAILED DESCRIPTION OF THE PREFERRED EMBODIMENT

Figure 1:
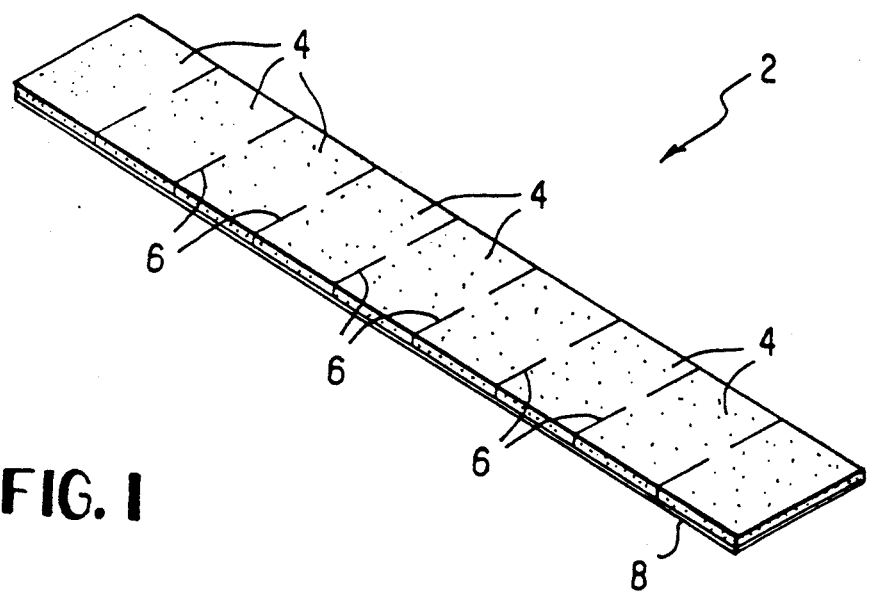
FIG. 1 is a perspective of a strip of finger protectors in accordance with the invention.

With reference to FIG. 1, a strip 2 of finger protectors comprises a plurality of individual protectors 4 which have been made from a strip of vinyl. The vinyl is scored as at 6 so that an individual protector may be easily torn from the strip 2.

The vinyl is provided with an adhesive backing 8 having a protective paper which may be removed. In the embodiment presently used, the adhesive is double sided tape with one surface secured to the vinyl.

As noted above, the primary material of the invention is flexible vinyl having a thickness of about 13 mils. The vinyl has been coated with a fungicide and has a slightly roughened upper surface. The protectors are square and about ¾" on each side.

Figure 2:
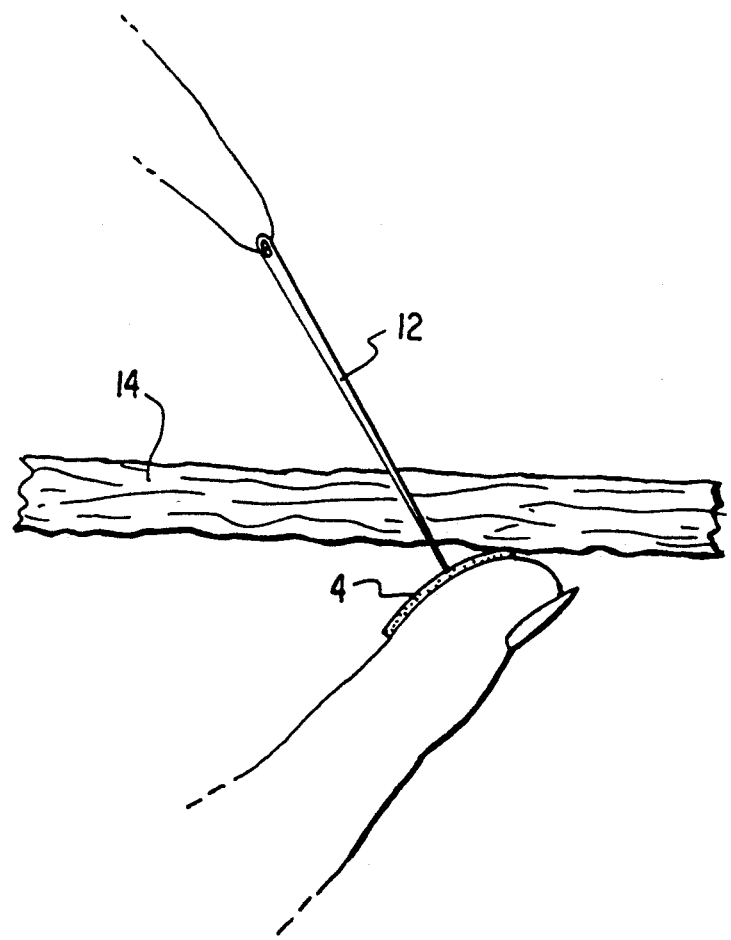
FIG. 2 shows a finger protector of the invention in use.

FIG. 2 shows the finger protector of the invention in use. An individual protector 4 has been removed from the strip 2 and the protective paper has been removed to expose the adhesive. The protector has then been applied to the pad of a finger 10 used as the under finger in quilting. A needle 12 has been pushed through the quilt 14 and is engaging the finger protector of the under finger of the quilter. The quilter may now push the tip of the needle upward to guide the needle back through the quilt while also pushing on the eye end of the needle with a thimble.

Modifications within the scope of the appended claims will be apparent to those of skill in the art.

I claim:

1. A method of quilting comprising the steps of:
    applying a protector to an underfinger of a quilter for protecting said underfinger, said protector comprising a pad of flexible vinyl material and having a rear surface completely covered by an adhesive backing for attaching said pad to said underfinger, wherein said material is thin enough to allow the quilter to feel the engagement between a tip of a needle and the material while preventing injury to the finger,
    passing a needle through a quilt in a first direction and engaging the tip of said needle with said protector, sensing engagement between said tip and said protector, and pushing on said tip with said protector and guiding said needle through said quilt in a second direction.

2. The method according to claim 1 wherein said step of applying said protector includes the step of tearing said protector from a strip of flexible vinyl having a plurality of score lines for dividing said strip into a plurality of said pad protectors and allowing each of said protectors to be easily torn from said strip, and applying said divided protector to the underfinger of the quilter.

3. A method according to claim 1 wherein the thickness of said material is about 13 mil.

* * * * *